United States Patent [19]
deVries

[11] Patent Number: 5,714,657
[45] Date of Patent: Feb. 3, 1998

[54] NATURAL GAS CONVERSION TO HIGHER HYDROCARBONS

[76] Inventor: Louis deVries, 1141 S. Eliseo Dr., Greenbrae, Calif. 94904

[21] Appl. No.: 792,230

[22] Filed: Jan. 31, 1997

Related U.S. Application Data

[63] Continuation of Ser. No. 487,602, Jun. 7, 1995, abandoned, which is a continuation-in-part of Ser. No. 368,789, Jan. 4, 1995, abandoned, which is a continuation-in-part of Ser. No. 212,167, Mar. 11, 1994, abandoned.

[51] Int. Cl.$^6$ ............................................. C07C 1/10
[52] U.S. Cl. ..................... 585/310; 585/638; 585/733; 518/702; 518/711
[58] Field of Search ........................... 585/310, 315, 585/408, 469, 638, 733; 208/950; 518/702, 711; 423/418.2

[56] References Cited

U.S. PATENT DOCUMENTS

| | | | |
|---|---|---|---|
| 2,274,064 | 2/1942 | Howard et al. | |
| 2,472,219 | 6/1949 | Lyons | |
| 2,579,663 | 12/1951 | Gilbert et al. | 260/449.6 |
| 2,786,863 | 3/1957 | Kölbel et al. | 260/449.6 |
| 3,723,344 | 3/1973 | Reynolds | 252/373 |
| 4,690,695 | 9/1987 | Doshi | 55/16 |
| 4,704,487 | 11/1987 | Devries et al. | 585/417 |
| 4,704,488 | 11/1987 | Devries et al. | 595/415 |
| 4,704,493 | 11/1987 | Devries et al. | 585/415 |
| 4,836,833 | 6/1989 | Nicholas et al. | 55/16 |

FOREIGN PATENT DOCUMENTS

| | | |
|---|---|---|
| 0291857 | 5/1988 | European Pat. Off. |
| 0355218 | 2/1990 | European Pat. Off. |
| 930 685 | 7/1955 | Germany |
| 1 034 164 | 7/1958 | Germany |
| 1 060 854 | 7/1959 | Germany |

OTHER PUBLICATIONS

Green et al., "Conversion of Natural Gas to Transport Fuels," Tecnol. Ciencia. Ed. (1991) 7:25–37.

Fox et al., "An Evaluation of Direct Methane Conversion Processes," Chemical Engineering Progress (1990) Apr.: 42–50.

Taylor & Noceti, "Conversion of Methane to Gasoline-Range Hydrocarbons," Proc. 9th Int'l Cong. on Catal. (1988) 11: 990–997.

Scurrell, "Prospects for the Direct Conversion of Light Alkanes to Petrochemical Feedstocks and Liquid Fuels," Applied Catalysis (1987) 32: 1–22.

Keim, "C$_1$ Chemistry: Potential and Developments," Pure & Applied Chem. (1986) 825–832.

Montgomery et al., "Thermodynamics and Stoichiometry of Synthesis Gas Production," Industrial & Engineering Chemistry (1948) Apr.: 601–607.

Schwob, "Fabrication du Méthanol. La rétroconversion du gaz carbonique, filière d'avenir," L'Actualité Chimique (1982) Jan.: 28–30. The non–catalytic, high temperature Reverse Water Gas Shift reaction described herein is also described in U.S. Patent No. 3,723,344.

Kölbel & Vorwerk, "Synthese von Kohlenwasserstoffen aus Kohlenoxyd und Wasserdampf," Brennstoff–Chemie (1957) 38:2–9. The catalytic process described herein is also described in U.S. Patent. No. 2,579,663 and 2,786,683.

*Primary Examiner*—Glenn Caldarola
*Assistant Examiner*—Bekir L. Yildirim
*Attorney, Agent, or Firm*—Burns, Doane, Swecker & Mathis LLP

[57] ABSTRACT

This patent is concerned with a unique process for converting natural gas into hydrocarbons. More particularly, it concerns a novel combination of processing steps wherein the natural gas is first converted into syn gas, the hydrogen of which is reacted with carbon dioxide to produce a mixture of water and carbon monoxide which is then contacted with a metal catalyst to give a mixture of hydrocarbons.

32 Claims, 5 Drawing Sheets

NATURAL GAS CONVERSION TO HIGHER HYDROCARBONS

This application is a continuation of application Ser. No. 08/487,602, filed Jun. 7, 1995, now abandoned, which is a continuation-in-part of application Ser. No. 08/368,789 filed Jan. 4, 1995 now abandoned which is a continuation-in-part of application Ser. No. 08/212,167 filed Mar. 11, 1994 now abandoned.

This application is a continuation-in-part of application Ser. No. 08/368,789 filed Jan. 4, 1995, which in turn is a continuation-in-part of application Ser. No. 08/212,167, filed Mar. 11, 1994.

INTRODUCTION

1. Technical Field

The field of this invention is production of higher hydrocarbons from syn gas.

2. Background

Natural gas is an abundant energy source and is the preferred fuel for many uses, including home heating and cooking, electricity generation, various manufacturings, etc. As such, there is a constantly increasing demand for natural gas. The term "natural gas" is used to describe a wide variety of gaseous mixtures. That is, natural gas from different fields varies in composition. In general, it varies from essentially pure methane to mixtures of methane with other gases, such as nitrogen, carbon dioxide, ethane, ethene, propane, hydrogen sulfide, dimethyl sulfide, and the like. In many cases, the chief diluent of the methane is carbon dioxide which may vary from very small amounts to quantities as great as 50% or more. The presence of gases other than methane affects the quality of the gas and in some cases may render the field unfit for commercialization.

Vast quantities of natural gas are available in many isolated regions of the world. Furthermore, natural gas is found in many inhospitable areas, such as deserts, Arctic regions, etc. As a result there is a well recognized need for converting natural gas into a liquid form for transportation to commercial centers. One method is cooling and compressing to a liquid product. This has been developed and is used commercially. However, this method requires expensive liquefaction plants and specially constructed tankers and/or pipe lines for distribution which are not feasible in many areas of the world.

A more preferred method for the "liquification" of natural gas is the one in which natural gas is converted into higher molecular weight hydrocarbons which are liquids at normal temperatures and pressures. Such products are as easily handled and transported as are any other liquid hydrocarbons. In spite of many years of research and development on this problem, there is still no generally accepted method for making a higher molecular weight liquid hydrocarbon from natural gas. Reviews of this problem are given in: (1) Tecnol. Ciencia Ed., 7, (1) 25–37 (1991), (2) Proceedings of the 9th Intl. Congress on Catalysis, 11, 990–996 (1988) and (3) Applied Catalysis, 32, 1–22 (1987).

Direct processes for converting natural gas into liquid hydrocarbons have been described in the literature and include oxidative coupling, partial oxidation and oxyhydrochlorination. See for example: Chem. Eng. Progr. pp 42–50 (April 1990).

U.S. Pat. Nos. 4,704,493 4,704,488 and 4,704,487 claim processes in which methane is directly converted into liquid aromatic mixtures by reaction over certain selected catalysts under rather specific conditions. However, yields are rather modest and much of the feed stock is lost to undesirable by-products.

To date, the preferred method of changing natural gas into a liquid form is to first convert it into synthesis gas. A mixture of carbon monoxide and hydrogen is commonly called synthesis gas or syn gas for short. This mixture is readily made by the partial oxidation of hydrocarbons such as methane, butane, and the like. Furthermore it may also be made by the steam hydrolysis of coal. In the present invention, the syn gas feed stock is preferentially made by the partial oxidation of natural gas. Many processes have been developed for converting syn gas into useful products, (see for example: Pure and Appl. Chem. 58, (6) pp. 825–832 (1986)).

Direct conversion of syn gas into hydrocarbons involves the hydrogenation of carbon monoxide into paraffins, olefins and oxygen containing products. There are three well known processes for the production of hydrocarbons from syn gas: the Fischer-Tropsch process, the Shell Middle Distillate process, and the Mobil methanol-to-gasoline process.

In the Fischer-Tropsch reaction the gaseous mixture of carbon monoxide and hydrogen is reacted in the presence of a promoted transition metal catalyst to produce a hydrocarbon mixture having a broad molecular weight distribution. This product is predominately straight chain, saturated hydrocarbons of low octane value. One big drawback of this process is the conversion of about 40% of the feed gases into methane. Furthermore, the reaction is highly exothermic, requiring heat disposal.

The Shell Middle Distillate Synthesis of hydrocarbons involves carrying out the Fischer-Tropsch reaction under conditions that produce a high molecular weight, waxy paraffinic product. This product is then catalytically cracked to yield predominantly fuel in the middle distillate range. Kerosene and gas oil fractions are also obtained. This process suffers from the same drawbacks as the Fischer-Tropsch reaction, plus it requires a second catalytic reactor with its attendant catalyst deactivation and regeneration problems.

The third process for converting syn gas into liquid hydrocarbons involves first the catalytic conversion of syn gas into methanol which is then further reacted in the presence of a second catalyst to produce hydrocarbons. This route is known as the Mobil MTG (methanol-to-gasoline) process. As disclosed in U.S. Pat. No. 4,595,702, Chu et al., the process requires two catalytic reactors. Since each reactor requires its own catalyst, deactivation and regeneration are a continuous problem.

Conversion of natural gas to syn gas followed by one of the three processes cited above is today the only useful route to liquid hydrocarbons from natural gas, although they are all far from satisfactory.

On the other hand, multicarbon hydrocarbons can be produced by the reaction of carbon monoxide and water over a metal catalyst at elevated temperatures. This process, the Koelbel-Engelhardt (K-E) reaction, is well known, having been studied by Koelbel and his associates for many years. See for example, U.S. Pat. Nos. 2,579,663 and 2,786,863 and German Patent Nos. 930,685 (1949), 1,034,164 (1958) and 1,060,854 (1956), Brennst.-Chem. 38,(1/2) pp 2–9 (1957) and Chapter 7 of "The Fischer-Tropsch Synthesis, edited by R. B. Anderson, Academic Press, 1984.

In this process, carbon monoxide and water, in a ratio of from 0.5:1 to 3:1 are passed over an activated metal catalyst at temperatures in the range of 200° to 400° C. The catalysts useful for this reaction are the solid synthesis catalysts such as those used in the Fischer-Tropsch reaction, preferably comprising metals of group VIII of the periodic table, especially iron, nickel and cobalt. These catalysts may be supported on any suitable support such as silica gel, alumina, kieselguhr, bauxite, etc. and may contain promoters such as the oxides of potassium, magnesium, calcium, thorium, or metals such as copper.

The drawback of this process for producing hydrocarbons economically has been the concurrent production of large amounts of carbon dioxide. For each atom of carbon monoxide converted into a hydrocarbon molecule, 2 atoms are converted into carbon dioxide. That is, 16 molecules of carbon dioxide are produced per molecule of an 8-carbon hydrocarbon. This much carbon dioxide of low economic value is not only a waste of starting material but is difficult to dispose. Venting to the atmosphere is contrary to good waste management in view of the belief that the air is already overloaded with this gas which may lead to global warming.

The present invention overcomes this drawback of the K-E process and produces multicarbon hydrocarbons from natural gas. This is accomplished by using integrated effluent processing to provide a cyclic process wherein the by-product carbon dioxide of the K-E reaction is reacted with syn gas obtained by partial oxidization of natural gas to produce a mixture of carbon monoxide and water for further processing in the K-E reaction.

SUMMARY OF THE INVENTION

My invention is an improvement in the process for preparing multicarbon hydrocarbons and carbon dioxide by the metal catalyzed reaction of carbon monoxide and water, which comprises heating said carbon dioxide with syn gas, preferably obtained by the partial oxidation of natural gas, at an elevated temperature to produce carbon monoxide and water useful as feed to said metal catalyzed reaction. Broadly, an efficient process is provided for converting natural gas into liquid hydrocarbons. In this process natural gas is partially oxidized to a syn gas having approximately a 2:1 ratio of hydrogen to carbon monoxide, the ratio preferred for the classical Fischer-Tropsch reaction. The hydrogen is separated from the carbon monoxide by reaction with carbon dioxide. The carbon monoxide is then reacted with water to produce liquid hydrocarbons and carbon dioxide. The carbon dioxide is then separated and reacted with the hydrogen in the syn gas to produce additional carbon monoxide and water. This then sets up a cyclical process in which oxygen and natural gas are the feed components and excess water and liquid hydrocarbons are the product components.

In summary, this is a process for converting natural gas into hydrocarbons comprising a novel combination of processing steps wherein the natural gas is first converted to syn gas, the hydrogen of which is reacted with carbon dioxide in a reverse water-gas shift reactor to produce a mixture of water and carbon monoxide which is then contacted with a metal catalyst in a reactor to give a mixture of hydrocarbons.

DESCRIPTION OF THE SPECIFIC EMBODIMENTS

Figure 1:
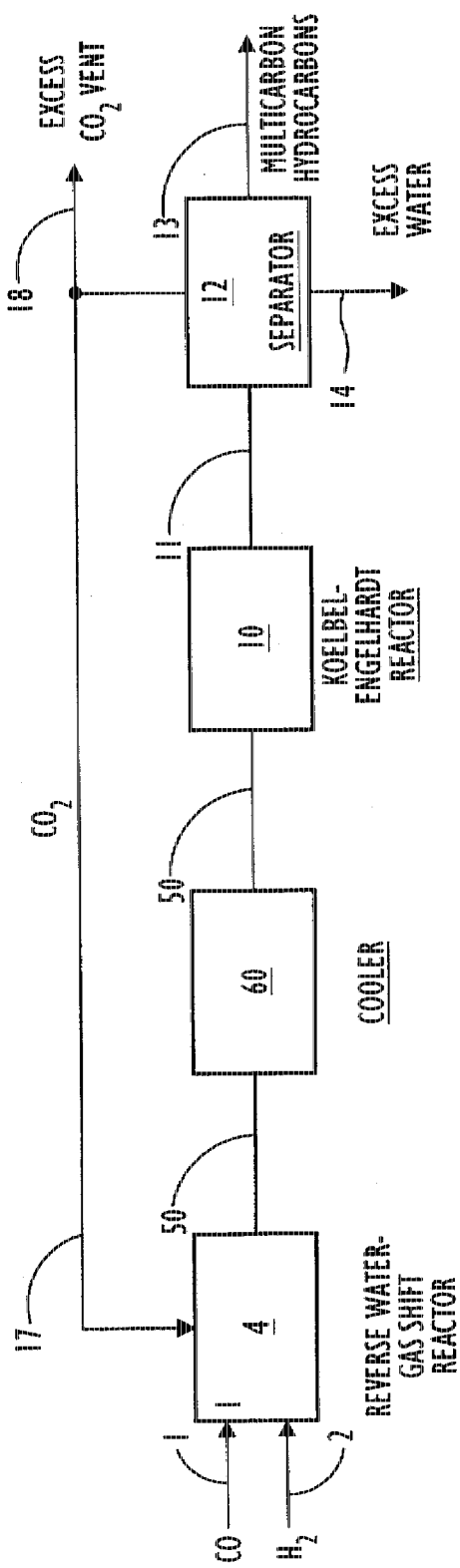
FIG. 1 is a block flow diagram of the subject process.

In the instant multi-step cyclic process, the term "return" shall mean the addition of a reaction product from a subsequent process to the feed of a previous process; and the term "recycle" shall mean the reintroduction of unreacted feed components from the reaction product of a reactor into the feed of said reactor.

In accordance with the subject invention, syn gas preferably obtained by the partial oxidation of natural gas, is converted to higher hydrocarbons, particularly $C_2+$ (two or more carbons per molecule), in high yield based on the amount of carbon source in the natural gas charged to the system. The methane in the natural gas is used as a source for the production of syn gas. The syn gas is reacted in a first reactor with carbon dioxide at elevated temperatures to produce additional carbon monoxide and water. The entire reaction product from the first reactor is then reacted in the presence of a metal catalyst in a second reactor to produce higher hydrocarbons, ($C_2+$) and carbon dioxide. These hydrocarbons are removed with any unreacted water from the second reactor effluent, leaving the second reactor remainder, all or a portion of which is returned to the first stage of the process. The desired liquid hydrocarbon product is isolated substantially free of non-hydrocarbon components.

In this process, the only carbon containing substances withdrawn from the cyclic process are the desired higher hydrocarbon products and the only carbon containing substance admitted is the carbon monoxide which is essentially quantitatively produced from the methane in the natural gas. Only sufficient carbon monoxide is charged to the process to produce the amount of hydrocarbons that are withdrawn. Carbon monoxide is never vented and carbon dioxide is vented only to balance any carbon dioxide being charged in the natural gas feed stock. Therefore, the cyclic process of my invention converts the methane in the feed essentially quantitatively into higher hydrocarbons.

A very important advantage of my process over the processes of the prior art is that natural gases containing relatively large amounts of carbon dioxide are satisfactory feed stocks. That is, natural gas with as much as 60% or more carbon dioxide will produce liquid hydrocarbons from the methane portion of the gas and at the same time give a separated stream of carbon dioxide. Therefore, the feedstocks will normally comprise at least 25 mole % methane, preferably at least about 35 mole % methane.

In addition, the total process is in large measure adiabatic, since the heat produced in the exothermic partial oxidation essentially balances the heat needed in the endothermic reaction between carbon dioxide and hydrogen. Accordingly very little, if any, natural gas is burned to supply this heat. This is superior to any of the prior art processes for making liquid hydrocarbons from natural gas, wherein large amounts of extra heat are required. Furthermore, the high heat capacity carbon dioxide produced in, and removed from, the second reactor provides an efficient way in which to help remove the excess heat released in the K-E reaction.

The effect of any inefficiencies in any stage of the process is to slow down the conversion of natural gas but not to diminish the yield of hydrocarbon product based on carbon charged from the natural gas. In addition, the movement of gases is efficient, minimizing the energy costs and wastes of moving large volumes of gases and having to heat large volumes of diluent gases which are not involved in the reaction of the different steps.

In more detail, my new invention is a process for the production of higher, i.e. multicarbon, hydrocarbons from a mixture of hydrogen and carbon monoxide gases, comprising the steps of:

(a) heating said mixture of gases with carbon dioxide in a first reactor at an elevated temperature to produce additional carbon monoxide and water, resulting in a first reactor effluent, (b) heating essentially all of said first reactor effluent in the presence of a metal catalyst in a second reactor wherein the carbon monoxide and water react to produce a second reactor effluent comprising multicarbon hydrocarbons and carbon dioxide, (c) separating the multicarbon hydrocarbons from said second reactor effluent and returning sufficient of said carbon dioxide in said second reactor effluent to said first reactor to maintain a predetermined level of carbon dioxide in said first reactor.

In the above process it is preferred to obtain the mixture of carbon monoxide and hydrogen from the partial oxidation of natural gas. It is also preferred to operate the first reactor with an essentially equimolar mixture of hydrogen and carbon dioxide or with a one molar excess of carbon dioxide over hydrogen. Finally, in the above process it is preferred to maintain the temperature in the first reactor above 800° C. The resulting preferred process may be further characterized as a process for the production of multicarbon hydrocarbons from natural gas comprising the steps of: (a) oxidizing said natural gas in a partial oxidizer to produce a syn gas, (b) heating said syn gas at a temperature above 800° C. in a first reactor with carbon dioxide, (c) reacting said reaction product of said first reactor in contact with a metal catalyst in a second reactor, (d) removing the hydrocarbons and excess water from the reaction product of the second reactor, (e) returning at least a portion of the remainder of the reaction product from the second reactor back to the oxidizer and (f) separating the desired hydrocarbon product from the water phase.

The multicarbon hydrocarbons prepared by the process of this invention are compounds of carbon and hydrogen having more than one carbon atom per molecule. The preferred hydrocarbons produced by the present process are liquid hydrocarbons having more than four carbon atoms per molecule. These latter compounds have boiling points in excess of 25° C. at atmospheric pressure. Hydrocarbons boiling below this value include ethane, propanes, propenes, butenes and butanes which are separated from the higher hydrocarbons. These lower molecular weight compounds have many uses, e.g. polymerization of the olefins to other higher molecular weight hydrocarbons, including high octane polymer gasoline and others may be oxidized to alcohols, etc. They may also be returned to the oxidizer for conversion into syn gas.

By reaction product is meant all of the material, including product, by-product and unreacted feed stock, passing out of a reactor, normally a gaseous effluent, and into any other piece of equipment as a single stream, usually being separated into at least two streams for further processing, until the final product is obtained.

The above described process may be modified in many ways without departing from the spirit of the invention. These modifications include the addition of a separation step between the first and the second reactors, recycling the material separated back to the first reactor, returning the carbon dioxide from the second reactor to the first reactor via the partial oxidizer, and variations in the work-up of the hydrocarbon product.

In the first reactor carbon dioxide is reacted with the hydrogen contained in the syn gas feed stock to produce water and more carbon monoxide. This reactor is maintained at an elevated temperature above about 500° C. preferably above 800° C. At this latter temperature, the equilibrium constant of the reverse water gas shift reaction has a value of 1 indicating an essentially even balance between the amounts of reactants and products. At higher temperatures, the equilibrium is shifted in favor of carbon monoxide and water. Lower temperatures may be employed but the reaction is slower and the amount of carbon dioxide converted to carbon monoxide is lowered.

The presence of hydrogen in the feed to the K-E reactor leads to a change in the hydrocarbon product mix, namely more saturated and more straight chain compounds and an increased amount of methane. At low hydrogen levels, below 20%, preferably below 10%, the change in hydrocarbon product is not significant. Thus, when the first reactor product is low in hydrogen a separation step is not necessary before passing the entire first reactor product into the second reactor. On the other hand with larger amounts of hydrogen, a separation step between the first and second reactor may be advantageous.

The hydrocarbon product of the second reactor contains a range of hydrocarbon molecules having from 1 to over 20 carbon atoms depending on the reaction conditions. In order to maximize production of liquid hydrocarbons the low boiling molecules may be allowed to remain in the gas phase of the product stream and returned to the first reactor along with the carbon dioxide. In a preferred embodiment, the carbon dioxide and any low molecular weight hydrocarbons are returned to the first reactor via the partial oxidizer. In this way the low molecular weight hydrocarbons are reoxidized to syn gas and fed to the first reactor.

Another way of handling the low molecular weight hydrocarbons is to first separate out all hydrocarbons and then distill off the low boiling compounds as a separate fraction. This fraction is then polymerized to produce more liquid hydrocarbons.

With these optional modifications in mind, my process may also be described as a process for the production of multicarbon hydrocarbons from natural gas comprising the steps of: (a) oxidizing said natural gas in a partial oxidizer to produce a syn gas, (b) heating said syn gas at a temperature above 800° C. in a first reactor with carbon dioxide, (c) separating essentially all of the carbon monoxide and water from the reaction product of said first reactor and recycling the remainder of said first reactor reaction product back to the first reactor, (d) mixing and reacting said separated carbon monoxide and at least 50% of said water in contact with a metal catalyst in a second reactor, (e) removing the hydrocarbons and excess water from the reaction product of the second reactor, (f) returning at least a portion of the remainder of the reaction product from the second reactor back to the oxidizer and (g) separating the desired hydrocarbon product from the water phase.

In the first reactor, the hydrogen of the syn gas mixture is reacted with carbon dioxide, in the absence of a catalyst, to produce more carbon monoxide. As used herein, about equimolar refers to a molar ratio of hydrogen:carbon dioxide in the range of 1.5:1 to 1:1.5. However, an excess of either hydrogen or carbon dioxide may be employed. The term excess refers to the relative ratio of the reactants. It is the amount of hydrogen or carbon dioxide in excess of the stoichiometric amount required for the reaction occurring in the first reactor, where stoichiometric is a 1:1 molar ratio. The molar excess of hydrogen or carbon dioxide in the first reactor ranges from 0.5 to 4 fold. Preferably there is a 2:1 mole ratio of carbon dioxide to hydrogen. Nevertheless, the mole ratio of hydrogen:carbon dioxide may range from 4:1 to 1:4. When a high proportion of excess reactant is used it is preferable to add a separation step between the first and second reactors. The decision as to which mode to employ in any given situation is determined by weighing the advantages of high conversion in the first reactor versus the sizes of the first reactor and the optional first separator.

The desired ratio of the two reactants in the first reactor is maintained by determining the amount of carbon dioxide in the syn gas feed stock and adjusting the amount of carbon dioxide returned from the second reactor back to the first reactor to allow for any carbon dioxide in the syn gas feed. In addition, when a separation step is practiced between the first and second reactors, the desired ratio is also maintained by recycling the remainder of the reaction product from the first reactor, after removing carbon monoxide and water, back to the first reactor.

When there is a separation step after the first reactor, the recycle stream from the first separator is mainly hydrogen and carbon dioxide, the relative amounts of each depending on the operating mode selected. When in the equimolar mode, the amounts of hydrogen and carbon dioxide in this recycle stream are essentially equal. In an excess mode, all of the excess gas is present in the recycle stream along with any unreacted species. Thus in all cases, with the above recycles in place, steady state operation is obtained by charging the syn gas at a constant rate. Furthermore, it is possible to provide an excess of hydrogen or carbon dioxide via the syn gas feed stock. For example, carbon dioxide contained in the natural gas feed to the oxidizer will contribute that much to the total carbon dioxide concentration in the first reactor. Carbon dioxide prepared by completely oxidizing natural gas with pure oxygen is another source. Excess hydrogen is obtained by increasing the amount of syn gas fed to the first reactor, or limiting the amount of carbon dioxide charged to the first reactor.

The remainder of the reaction product from the second reactor after separation of the hydrocarbons and water is a gas, and is essentially carbon dioxide with small amounts of hydrogen and methane. Some or all of this gaseous material is returned to the first reactor, preferably via the oxidizer. The amount returned depends on the amount of carbon dioxide in the natural gas feed stock. As the concentration of carbon dioxide in the natural gas increases, the amount of the gaseous material returned to the first reactor or to the oxidizer, decreases until the two quantities balance at about 66% carbon dioxide in the natural gas. In the oxidizer, any low molecular weight hydrocarbons are oxidized to syn gas and most of the carbon dioxide passes through unchanged. It is known that the presence of carbon dioxide in a partial oxidizer limits the formation of soot.

The process occurring in the first reactor is the non-catalytic, high temperature Reverse Water Gas Shift reaction, i.e. $H_2 + CO_2 \rightarrow CO + H_2O$. The reverse water gas shift reaction is in equilibrium with the water gas shift reaction. Above 800° C. the reverse reaction is thermodynamically favored and proceeds without the need for a catalyst. A description of this reaction is given in U.S. Pat. No. 3,723,344 and in L'Actualite Chimique, pp 28–30 (January 1982).

The process occurring in the second reactor is the catalytic Koelbel-Engelhardt reaction, i.e. $3CO + H_2O \rightarrow 2CO_2 +$ ----$(CH_2)$---- where---- ----$(CH_2)$---- is the building block for higher hydrocarbons. This process is described for instance in U.S. Pat. Nos. 2,579,663 and 2,786,863 and in German Patent Nos. 930,685 (1949), 1,034,164 (1958) and 1,060,854 (1956), in Brennst.-Chem. 38,(1/2) pp 2–9 (1957) and in Chapter 7 of "The Fischer-Tropsch Synthesis", edited by R. B. Anderson, Academic Press, 1984. All of the above citations are hereby incorporated by reference. From the preceding equation it is obvious that the Koelbel-Engelhardt reaction per se is incapable of carbon monoxide conversions to hydrocarbons exceeding 33.3% since 66.6% of the carbon monoxide is converted to carbon dioxide. In the prior art, this carbon dioxide is invariably vented.

However combination of the Koelbel-Engelhardt and the Reverse Watergas Shift reactions in the cyclic process of the instant invention allows near quantitative conversion of the carbon monoxide and consequently of the methane in the feedstock to liquid hydrocarbons. This is surprising and is quite a change from the prior art processes wherein 60% yields of hydrocarbons, based on methane in the feed stock, are exceptional. The hydrocarbons produced by this reaction are mixtures of straight chain, branched and cyclic hydrocarbons preferably having at least 5 carbon atoms per molecule (i.e. $C_{5+}$). For each carbon number, there are both saturated and unsaturated isomers. The hydrocarbon fraction in the gasoline boiling range has high octane value and is useful as gasoline. Thus the process of the present invention overcomes two of the drawbacks of the prior art, i.e. low yields of saturated hydrocarbons of straight chain structure.

Under some extreme reaction conditions, the product may contain small amounts of oxygenated compounds such as alcohols, ketones, etc. Usually the product has less than 5 mole percent of oxygen containing compounds. When operating under the preferred conditions of this process, less than 2 mole percent of oxygen containing compounds are produced. As used throughout this disclosure, the term liquid hydrocarbons refers to a product that is a major amount of hydrocarbons but may contain from 0 to 5% of oxygen containing compounds.

When using natural gas feed stock, the first step in this process is the conversion of natural gas to syn gas. The preferred method of preparing syn gas feed stock from natural gas or methane is by a partial oxidation process. This partial oxidation process is well described in: Ind. and Eng. Chem. 40 (4) 601–607 (1948).

In the preferred mode of the present invention, the heat produced by the oxidation of natural gas to syn gas essentially balances the heat required by the reaction occurring in the first reactor. In the event that insufficient heat is obtained by the oxidation of the natural gas feed, additional higher molecular weight hydrocarbons can be added to the oxidation feed. These higher molecular weight hydrocarbons include ethane, propane, butane and the like. Some or all of these may be in the return from the second reactor.

An integral part of the instant invention is control of the relative ratio of hydrogen to carbon dioxide in the first reactor. Hydrogen is charged to the first reactor in the syn gas feed stock in a fixed ratio to carbon monoxide. But the ratio of reactants is determined by the amount of carbon dioxide charged to the first reactor. The carbon dioxide in the first reactor is mainly obtained by returning from 0 to 100% of the carbon dioxide made in the second reactor back to the first reactor. The amount of carbon dioxide returned from the second reactor depends on the amount of carbon dioxide charged directly or via the syn gas feed stock.

It is preferred to operate with about a 2:1 mole ratio of carbon dioxide to hydrogen in the first reaction zone. But in the high excess gas mode, the excess hydrogen or carbon dioxide in the reaction product of the first reactor is separated and recycled back to the first reactor, thereby initially creating and then maintaining an excess of cycling hydrogen or carbon dioxide within that reactor.

PROCESS DESCRIPTION

In the following discussion, methane ($CH_4$) is used in the chemical equations to exemplify natural gas. These equations are idealized but are not unrealistic.

The reaction occurring in the partial oxidizer is well known and gives a hydrogen to carbon monoxide mole ratio of 2:1, as is shown by the following chemical equation:

$$2CH_4 + O_2 \rightarrow 4H_2 + 2CO \quad (1)$$

It is preferred to charge to the first reactor, syn gas containing hydrogen and carbon monoxide in a ratio of 1:1 to 3:1, preferably 2:1. Other gases may be present in the syn gas feed, for example, carbon dioxide, nitrogen, etc. However, sulfur-containing gases can not be tolerated in the catalyzed second reaction zone and must be removed from the process stream prior to that time. This separation may be effected before or after the oxidizer, or after the first reactor.

In the first reactor, the syn gas feed, preferably from the partial oxidation of natural gas, containing carbon monoxide and hydrogen, is reacted with carbon dioxide to produce water and additional carbon monoxide. The carbon dioxide in the outlet gasses of the first reactor may be recycled into the first reactor along with the syn gas, but the carbon dioxide in the off gasses of the second reactor may contain lower hydrocarbons and is preferably returned via the oxidizer. Additional carbon dioxide may have been in the natural gas charged to the oxidizer, or alternatively it may originate from the burning of natural gas with pure oxygen. The carbon dioxide may come from any or all of these sources. In any case the amount charged to the first reactor is regulated so as to maintain the preferred ratio of hydrogen to carbon dioxide as described above. This is preferably done by controlling the amount of carbon dioxide added via the return from the second reactor.

The thermal Reverse Water Gas Shift reaction taking place in the first reactor is carried out at a temperature within the range of 500° C. to 1800° C., preferably 800° C. to 1300° C., and most preferably about 800° C. to 1100°C. and at a pressure within the range of 1 to 350 atm., preferably 40 to 200 atm. Contact times are within the range of 0.05 to 5 seconds, preferably 0.1 to 2 seconds. This reaction is entirely thermal, a catalyst is not needed. Under these conditions, the mixture of carbon monoxide, hydrogen and carbon dioxide is largely converted into a mixture of water and carbon monoxide, any excess of cycling hydrogen or carbon dioxide remaining intact. This is shown by the following chemical equations where in equation (2) there is a 1:1 ratio of hydrogen to carbon dioxide, in equation (3) there is a 4:1 excess of hydrogen over carbon dioxide in the first reactor and in equation (4) there is an 4:1 excess of carbon dioxide over hydrogen in the first reactor:

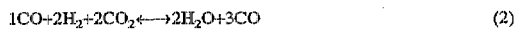
$$1CO + 2H_2 + 2CO_2 \longleftrightarrow 2H_2O + 3CO \quad (2)$$

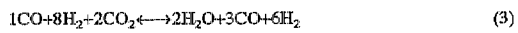
$$1CO + 8H_2 + 2CO_2 \longleftrightarrow 2H_2O + 3CO + 6H_2 \quad (3)$$

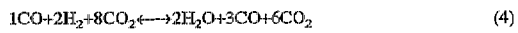
$$1CO + 2H_2 + 8CO_2 \longleftrightarrow 2H_2O + 3CO + 6CO_2 \quad (4)$$

The reaction product of the first reactor, i.e. a mixture of water, carbon monoxide, unreacted hydrogen and carbon dioxide, is then passed into the second reactor. When large excesses of one or the other reactant are utilized, it is preferred to pass the product of the first reactor through a separator in which carbon monoxide and water are isolated from the remainder of the reaction product, which remainder is recycled to the first reactor.

High purity carbon monoxide is selectively isolated from a gas mixture by any one of several processes. For example: (1) the Pressure Swing Adsorption process and (2) the COSORB absorption process. Either process is satisfactory for use in the present invention, however, the COSORB process is preferred. In both of these processes the gas feed containing carbon monoxide must be dried to less than about 1 ppm water.

The pressure (or vacuum) swing adsorption separation is well known and is described in U.S. Pat. Nos. 4,836,833 and 4,690,695 and in Gas Separation and Purification 5, 241 (December 1991).

The COSORB (carbon monoxide absorption) process is also well known. The carbon monoxide containing gas is passed into a toluene solution of a cuprous chloride-aluminum chloride complex at ambient temperatures. The carbon monoxide is bound into the complex and the remaining gasses pass through the solution unchanged. The carbon monoxide is recovered by heating the toluene solution. See for example: Chem. Eng. Prog. 70(5), (1974) and Chem. Economy and Eng. Rev. 9(12), 29 (December 1977).

A recent modification of the carbon monoxide absorption process uses a cuprous chloride-meta-toluidine complex in a glycol ether solvent. In this modification, the feed gas does not have to be dry. Ref. World Patent 15823 (1993).

The presence of hydrogen in the feed to the Koelbel-Engelhardt reactor negatively affects the quality and yield of the hydrocarbon product of this process. Any hydrogen present in this reactor reduces half of an equivalent molar amount of carbon monoxide via a Fischer-Tropsch reaction to produce hydrocarbons. For best results in the present process, the feed stock to the second reactor preferably has a carbon monoxide:hydrogen ratio greater than 4:1, preferably greater than 9:1.

Low concentrations of hydrogen in the feed to the second reactor are obtained by having (1) a high conversion of hydrogen in the first reactor and/or (2) an efficient procedure to separate unreacted hydrogen in the first reactor effluent from carbon monoxide. High conversions of hydrogen are obtained by operating at higher temperatures and in the excess carbon dioxide mode. These high conversions are obtained at the cost of an increase in reactor size and the need for a gas separator. In the excess hydrogen mode, the preferred method of lowering the hydrogen concentration is through the use of a gas separation procedure such as the COSORB process, rectisol process, or other similar processes which produce essentially pure carbon monoxide.

The water, produced in the first reactor and condensed out when a separation step is utilized is essential for the last step of the instant process wherein carbon monoxide and water are converted into liquid hydrocarbons. Since that reaction is a catalytic reaction, all material charged to it must be of high purity. This is especially true of the water, which must be free of any dissolved minerals. The water produced by the Reverse Water Gas Shift reaction meets this criterion. One of the advantages of the present invention is that the water produced in the first reactor is more than enough for reaction in the second reactor. A further advantage is that the carbon dioxide produced in the second reactor is the stoichiometric amount needed in the first reactor.

In the second reactor the water and carbon monoxide feed are converted into a mixture of carbon dioxide and hydrocarbons as shown in the following chemical equation:

$$1H_2O + 3CO \rightarrow 1-(CH_2)-+2CO_2 \quad (5)$$

wherein —(CH$_2$)— represents the elementary building block of higher hydrocarbons having the formula $C_nH_{2n}$ or $C_nH_{2n+2}$ where n is from 2 to about 20.

The feed mixture ratio to this reaction, of carbon monoxide and water, varies depending upon the catalyst present. In general, iron based catalysts require a carbon monoxide:water mole ratio of at least 2:1, preferably 3:1 whereas with cobalt based catalysts the preferred ratio is 3:2. This adjustment, if necessary, is made by condensing out a portion of the water produced in the first reactor or by revaporizing water in the previous step of the process in which a separation is carried out.

The process occurring in the second reactor known as the Koelbel-Engelhardt reaction, is carried out over a metallic catalyst. Those catalysts known for catalyzing the Fischer-Tropsch reaction are useful in this reaction. These catalysts are primarily the transition metals of the eighth sub-group of the periodic table of elements, namely, iron, nickel, and cobalt. Other metals which can be used include ruthenium, manganese and thorium. Alloys of these metals are also satisfactory catalysts. The catalysts may be supported on any suitable support such as talc, diatomaceous earth, silica gel, alumina, activated carbon, bauxite, kieselguhr and the like. Catalysts may also contain promoters, such as the oxides, hydroxides and salts of the alkali and alkaline earth metals such as sodium, potassium, rubidium, etc. Other promoters are the difficult to reduce metal oxides, such as alumina, potassium oxide, calcium oxide, thorium oxide and magnesium oxide. Compounds of vanadium, boron, copper and silver may also be used as promoters.

The preferred catalysts are based on cobalt, nickel or iron. Cobalt has advantages such as its oxidation resistance and ease of regeneration upon carbiding, as occurs when the gas feed to the reaction has more than a 3:1 ratio of carbon monoxide:water. To prevent carbiding of cobalt catalysts it is preferred to operate with a feed stock having a 0.3:1 to 2.8:1, preferably about 1.5:1 mole ratio of carbon monoxide to water. The cobalt based catalysts are much more tolerant of carbon dioxide in the feed than are the iron based catalysts. Furthermore, cobalt based catalysts produce hydrocarbons having a high degree of unsaturation, thereby producing feed stocks for a variety of processes and products, e.g. polymerization or detergent manufacture. Iron based catalysts are superior to the cobalt based catalysts in some respects, i.e. under identical conditions the reaction rate is higher for the iron catalyst. However, the iron catalyst is easily oxidized by excess water and the ratio of carbon monoxide:water must be 2:1 or greater. Iron catalysts are much more sensitive to carbon dioxide contamination because they are oxidized by carbon dioxide.

Before use in this process the metal catalyst is preferably activated. Activation is accomplished by heating the metal under reducing conditions. One way to activate the iron catalyst is by contacting it with a 1:2 carbon monoxide:hydrogen gas mixture by volume at a space velocity of 100/hour and at 230° C. for 70 hours. A cobalt catalyst may be activated by contact with a gas mixture of 20% carbon monoxide and 80% nitrogen at 170° C. for 55 hours. Other metal catalysts are activated under similar conditions as described in the prior art.

The reactor may contain a fixed bed of the metallic catalyst or employ a fluidized bed. A liquid phase reactor may also be utilized. Reaction temperatures are within the range of 150° C. to 400° C., preferably from 180° C. to 300° C. and most preferably about 230° C. Pressures in the reactor range from 1 atm. to 100 atm., preferably from 5 atm. to 50 atm. and most preferably about 10 atm. The gases are passed through the reactor at a space velocity dependent upon the catalyst. For example, with an unpromoted cobalt or an iron catalyst, useful space velocities are from 10 to 200/hr, preferably 10 to 100/hr and most preferably, 20 to 50/hr. For promoted cobalt catalysts, the space velocity must be such that a single pass over the catalyst gives over 50% preferably over 95% conversion of carbon monoxide. The corresponding range of space velocities is from about 10 to 1000/hr.

The reaction product stream from the second reactor, comprising a mixture of hydrocarbons, carbon dioxide, some hydrogen and unreacted water, is passed into a separator wherein the multicarbon hydrocarbons and water are separated from the gaseous carbon dioxide and volatile hydrocarbons. This separation may be carried out by cooling and condensing out the water and the higher hydrocarbons, leaving carbon dioxide and volatile hydrocarbons. The carbon dioxide may then be separated from the low boiling hydrocarbons such as ethane, ethene, propanes, propenes, butanes, butenes etc. by scrubbing with an aqueous solution containing a carbon dioxide absorbent, e.g. 10 to 20% monoethanolamine. Carbon dioxide absorption is at relatively low temperatures where it is converted into a carbonate. After removal of the insoluble volatile hydrocarbons, carbon dioxide is regenerated by heating the carbonate containing solution to about 100° C. (Chem. Eng. Progr. October 1986 pp. 38–46). Carbon dioxide may also be separated from low boiling hydrocarbons by utilizing the Rectisol process wherein the gas stream is passed through cold methanol to absorb the carbon dioxide. Heating the resulting solution releases the carbon dioxide for return to the first reactor, optionally via the partial oxidizer (Ref. "Catalysis, Science and Technology," vol 1, chapter 4 page 170, edited by J. R. Anderson and M. Boudant. Springer-Verlag (1981)). The unsaturated hydrocarbons isolated from this low boiling fraction by either of the above processes, may then be polymerized by contact with an appropriate catalyst to produce additional liquid hydrocarbons of more than 4 carbon atoms per molecule.

On the other hand, the low boiling hydrocarbons may not be separated from the carbon dioxide, but rather remain in the gaseous carbon dioxide stream. In this case the gaseous by-product material remaining after separation of the liquid hydrocarbons and excess water is a mixture of carbon dioxide, a small amount of hydrogen, and low molecular weight hydrocarbons. From 0 to 100% of this material is returned to the first reactor, preferably via the oxidizer. The quantity returned depends on the concentration of carbon dioxide in the natural gas fed to the oxidizer. Thus, when the natural gas is essentially free of carbon dioxide, all of the by-product material is returned because all of the carbon dioxide is needed in the first reactor. As the amount of carbon dioxide in the natural gas increases, the amount of by-product material returned is decreased so that the total carbon dioxide concentration in the first reactor is constant. Excess carbon dioxide vented from the second reactor may be collected for other uses such as enhanced oil recovery, carbonation, etc. Because of carbon dioxide return, the yield of hydrocarbons is effectively 100% based on the methane in the natural gas fed to the process.

The liquid hydrocarbons are readily separated from the excess water by decanting or other similar phase separation techniques. These hydrocarbons have an atmospheric pressure boiling point from about 25° C. to about 300° C. This range of boiling points indicates a hydrocarbon product having from 5 to 20 carbons per molecule, which are for the most part aliphatic and may be saturated or unsaturated.

A more complete understanding of the invention may be had by reference to the accompanying schematic drawing, FIG. 1, which illustrates the process of this invention. Referring now to FIG. 1. This figure is a block flow diagram of the basic process of the instant invention. In FIG. 1, a syn gas feed stock comprising carbon monoxide in line 1 and hydrogen in line 2 is charged to reactor 4. At the same time return carbon dioxide is charged to reactor 4 via line 17. Reactor 4 is a Reverse Water Gas Shift Reactor maintained at an elevated temperature, preferably in excess of 800° C. The reaction product from reactor 4 is passed via line 50 through cooler 60 and line 51 to reactor 10. Reactor 10 is a Koelbel-Englehardt reactor containing a metallic catalyst and operating at elevated temperatures of about 220°–250° C. The reaction product from reactor 10 is passed to separator 12 via line 11. In separator 12 any excess water is removed via line 14. Multicarbon hydrocarbon product is removed via line 13 and the carbon dioxide by-product is returned to reactor 4 via line 17. Excess carbon dioxide is vented through line 18.

Figure 2:
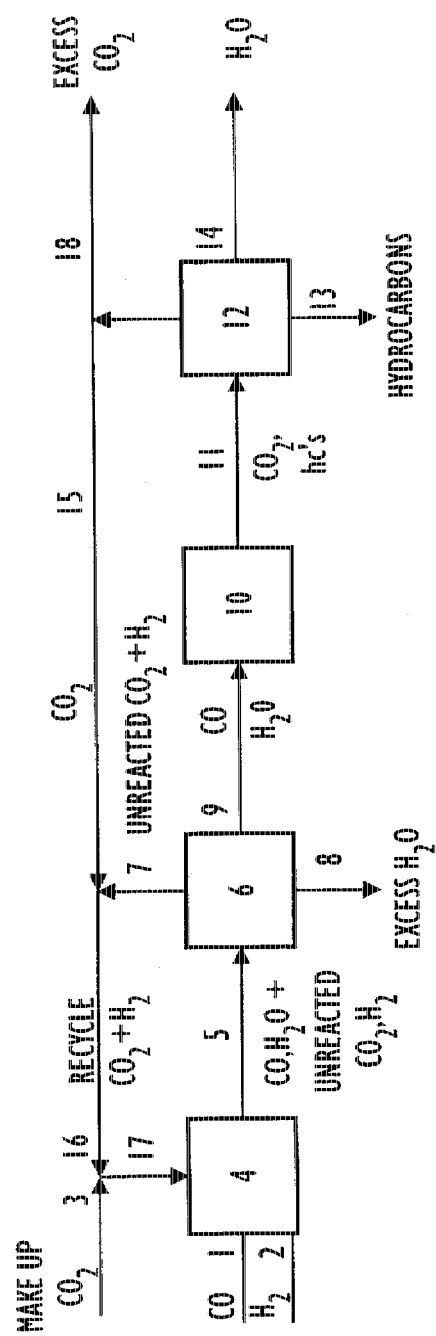
FIG. 2 is a block flow diagram of the subject process in which a separation step is inserted between the first and the second reactor.

Referring now to FIG. 2. This figure is a block flow diagram of the basic process of the instant invention in which a separation step has been added between the first reactor and the second reactor. In FIG. 2, a syn gas feed stock comprising carbon monoxide in line 1 and hydrogen in line 2 is charged to reactor 4. At the same time carbon dioxide is charged to reactor 4 via line 17 optionally comprising fresh carbon dioxide from line 3, and return as well as recycle carbon dioxide from line 15 and 16. Reactor 4 is a Reverse Water Gas Shift Reactor maintained at a temperature in excess of 800° C. The reaction product from reactor 4 is passed to separator 6 via line 5. In separator 6, carbon monoxide and water are separated from the remainder of the reaction product. Unreacted gases, are recycled to reactor 4 via lines 7, 16 and 17. Any excess water is removed through line 8. The remaining water and carbon monoxide are fed into reactor 10 through line 9. Reactor 10 is a Koelbel-Engelhardt reactor containing a metallic catalyst and operating at elevated temperatures in the range of 150° C. to 400° C. The reaction product from reactor 10 is passed to separator 12 via line 11. In separator 12 any excess water is removed via line 14. Multicarbon hydrocarbon product is removed via line 13 and the carbon dioxide by-product is returned to reactor 4 via lines 15, 16 and 17. Excess carbon dioxide is vented through line 18.

Figure 3:
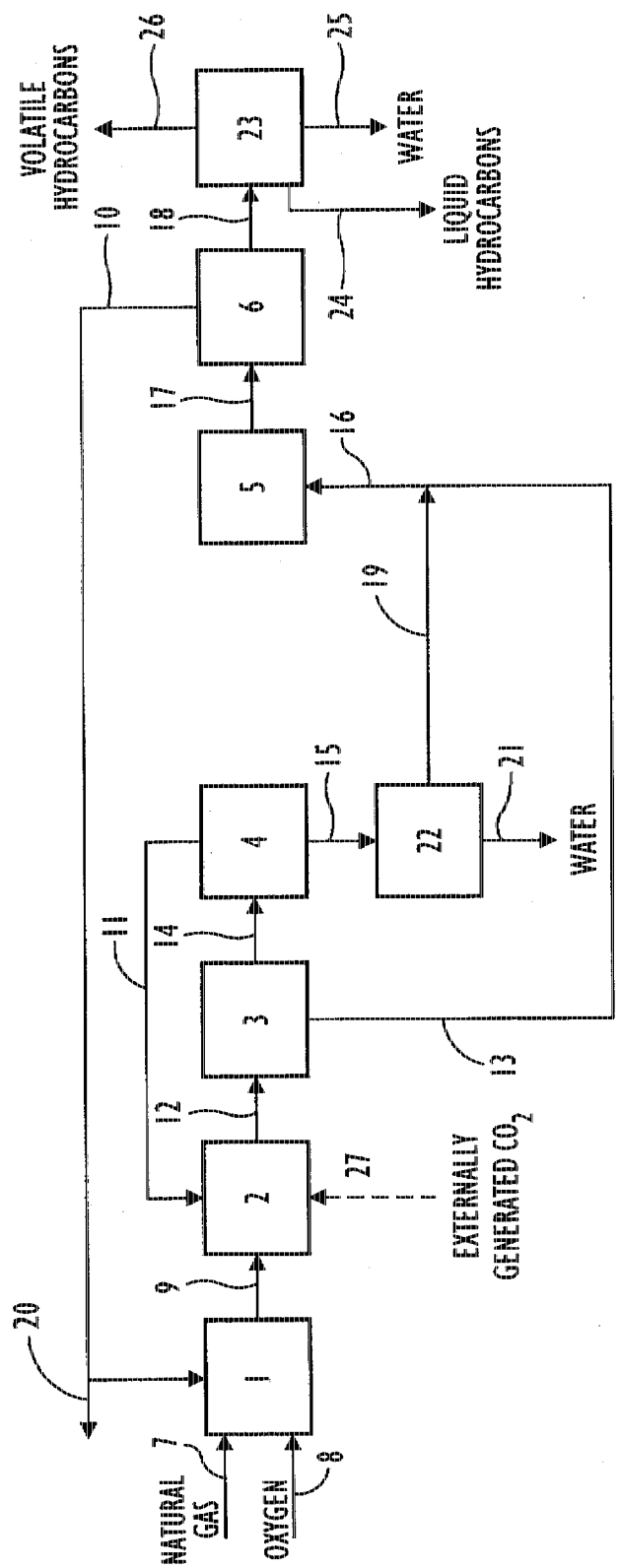
FIG. 3 is a block flow diagram of the subject process with a natural gas partial oxidizer and a separation step between the first and second reactors.

Referring now to FIG. 3. This figure is a block flow diagram showing in a simplified manner how the steps of the present process, operating with equal amounts of carbon dioxide and hydrogen in the first reactor, are coordinated with recycle of unreacted feed components and return of by-product streams to achieve essentially complete conversion of the carbon in the natural gas feed into a mixture of liquid hydrocarbons.

In FIG. 3, the natural gas feed stock to the cyclic process of the present invention is essentially 100% methane. This natural gas is fed to oxidizer 1 via line 7 while oxygen is fed to it via line 8. At the same time, under conditions of full recycle, carbon dioxide and optionally low molecular weight hydrocarbons from condenser 6 are charged into oxidizer 1, via line 10. In oxidizer 1, the natural gas and the returned low boiling hydrocarbons are partially oxidized to syn gas. The syn gas product of oxidizer 1 and carbon dioxide from the sources mentioned above are then passed via line 9 to the Reverse Water Gas Shift reactor, 2. Hydrogen and carbon dioxide from condenser 4 are recycled to reactor 2 via line 11. If needed, externally generated $CO_2$ may be added via line 27.

The reaction product mixture from reactor 2 is passed via line 12 to a separator 3. The gaseous carbon monoxide is removed from separator 3 via line 13. The water, hydrogen and carbon dioxide from separator 3 are removed via line 14 and charged to condenser 4. The liquid water formed within this condenser is removed via line 15, and after revaporization in vaporizer 22, it is removed through line 19 and is combined with the carbon monoxide in line 13 and then charged to reactor 5 via line 16. When an iron catalyst is used in reactor 5, half of the water remains in vaporizer 22. However, when a cobalt catalyst is used therein, all of the water is removed and charged to reactor 5 via line 19. Any excess water remaining in vaporizer 22 is removed via line 21. The hydrogen and carbon dioxide remaining after water separation in condenser 4, are removed and passed back to reactor 2 via line 11.

The reaction product from reactor 5 is passed into condenser 6 via line 17. In condenser 6, the hydrocarbons having a boiling point above 25° C. as well as excess water are separated from the more volatile components of the reaction product by cooling the reaction product mixture to about 10° C. The liquified material, comprising water and all hydrocarbons having 5 or more carbon atoms per molecule, is removed via line 18 and sent to phase separator 23. In this separator, the upper hydrocarbon phase is removed via line 24 and the aqueous phase is removed via line 25. The remainder of the reaction product mixture in condenser 6, consisting mainly of carbon dioxide, with some hydrogen and low boiling hydrocarbons is recycled back to reactor 1 via line 10. This procedure is preferred when the process is producing a negligible quantity of volatile hydrocarbons. However, when the process is operating to give appreciable quantities of volatile hydrocarbons, it is preferred that the recycle gas from condenser 6 be first passed into an aqueous solution of monoethanolamine wherein the carbon dioxide is absorbed and the volatile hydrocarbon gases are easily removed via line 26. Carbon dioxide is then recovered by heating the absorbent solution to the boiling point. The resulting vapor is cooled to condense the water. The thereby liberated carbon dioxide is then sent back to the oxidizer. Under some conditions of operation, excess carbon dioxide is removed through line 20.

Figure 4:
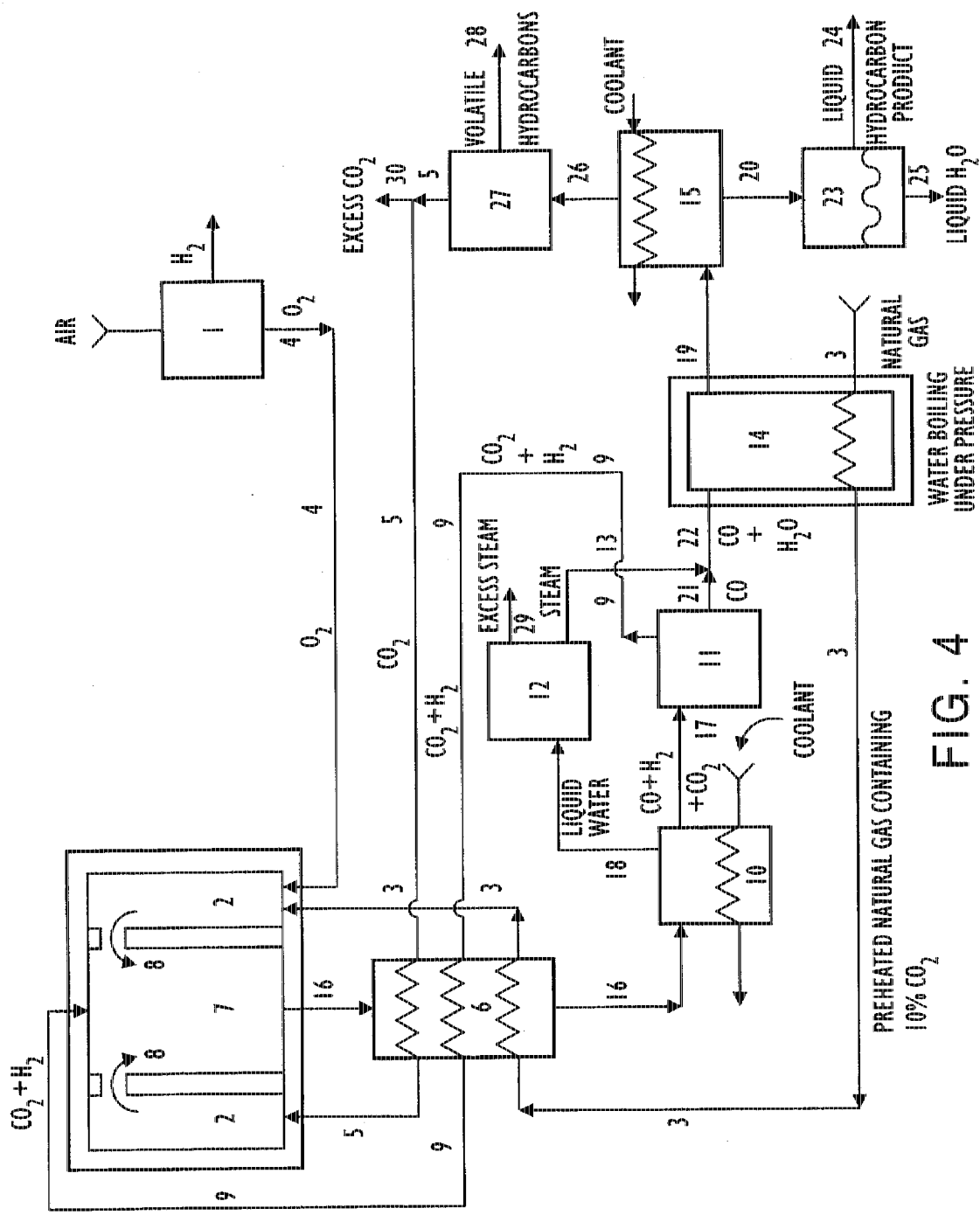
FIG. 4 is a detailed flow diagram of the subject process reacting carbon dioxide and hydrogen in equimolar amounts in a first reactor while feeding methane containing 10% carbon dioxide to the oxidizer.

A more detailed embodiment of the present invention utilizing (1) a separation step after the first reactor and (2) a separation of low molecular weight hydrocarbons from carbon dioxide in the reaction product of the second reactor is illustrated in the accompanying schematic drawing, FIG. 4. In this example, equimolar amounts of carbon dioxide and hydrogen are employed along with a cobalt catalyst. Referring now to FIG. 4, the following discussion describes the manufacture of multicarbon hydrocarbons by applying the process of the instant invention to a natural gas consisting of 90% methane and 10% carbon dioxide.

Oxygen separation from air via membrane-pressure swing adsorption processing is well known and produces oxygen having less then 10% nitrogen. For this example, 95+% oxygen is produced in reactor 1, removed via line 4 and charged to reactor 2. Natural gas, containing 10% carbon dioxide, is fed into the system via line 3 and is heated to about 900° C. by passing through reactor 14 and multiple heat exchanger 6. The oxygen and heated natural gas in volumetric ratio of about 0.5 are introduced into noncatalytic partial combustion reactor 2 operating at a temperature of 1100° C. under a pressure of 10 atmospheres. At the same time, carbon dioxide from condenser 15 via line 5 and through multiple heat exchanger 6, is charged to the oxidizer 2.

One method of utilizing the heat generated during oxidation for heating the subsequent carbon dioxide/hydrogen reaction is by the use of two concentric reactors. The outer reactor being the partial oxidation zone and the inner reactor being the Reverse Water Gas Shift Reaction zone as shown in FIG. 4, vessels 2 and 7.

The effluent from oxidizer 2, carbon monoxide, hydrogen and recycle carbon dioxide are passed into the Reverse Water Gas Shift converter 7, via ports 8. At the same time recycle carbon dioxide and hydrogen from COSORB separator, 11, heated by passing through the multiple heat exchanger 6, is fed to converter 7 via line 9. The converter 7 is maintained at a temperature of 1100° C. by the heat generated in the partial oxidation reaction occurring in the surrounding reactor 2. In vessel 7 the hydrogen:carbon dioxide ration is 1:1.

The product stream from reactor 7 in line 16 has the following composition: carbon monoxide=35.4%, carbon dioxide=20.3%, hydrogen=20.4% and water=23.9%. It is cooled by passing through the multiple heat exchanger 6 and cooler, 10. In this cooler, the bulk of the water is condensed and removed through line 18. The remaining product gas stream from cooler 10 is charged via line 17 to the carbon monoxide separator 11. In COSORB separator 11, the gas feed is dried to less then 1 ppm of water, then the carbon monoxide is separated from the carbon dioxide and hydrogen by adsorption in an aromatic solvent solution containing an aluminum trichloride/cuprous chloride complex. The unabsorbed carbon dioxide and hydrogen are removed from separator 11 via line 9. The carbon monoxide containing solution in separator 11 is heated to regenerate carbon monoxide which is removed via line 21.

The gaseous carbon dioxide and hydrogen in line 9 are passed through the multiple heat exchanger 6 wherein the temperature is raised to about 900° C., and is then recycled to the noncatalytic converter 7.

The water from line 18 is vaporized by heating to 100° C. in vaporizer 12. All of the steam generated in vaporizer 12 is added through line 13 to the carbon monoxide stream in line 21 to give a combined mixture having a 3:2 carbon monoxide:water ratio which is preferred for cobalt catalysts. This mixture is charged through line 22 to the Koelbel-Engelhardt reactor, 14 at a space velocity of about 30 per hour. Reactor 14 is maintained at 230° C. and 10 atmospheres. Reactor 14 is kept at the desired temperature by boiling water under pressure in a reactor jacket.

Reactor 14 is charged with a cobalt-thorium oxide-magnesium oxide-silicon dioxide catalyst containing 100 parts of cobalt, 5 parts of thoria, 10 parts of magnesia and 100 parts of silica. The catalyst is activated by heating for two hours at 450° C., with hydrogen gas passing over it at a space velocity of 1000/hr.

When steady state conditions are reached in reactor 14, samples of reactor effluent show a total conversion of carbon monoxide of about 98%. Gas chromatographic analysis shows that the hydrocarbon portion contains over 95% hydrocarbons having more than 4 carbon atoms.

The reaction product stream from reactor 14 is passed into condenser 15 via line 19. In this condenser, the temperature of the reaction product is lowered to 5° C., causing the hydrocarbons having more than 4 carbon atoms and the water present to condense and pass out of the condenser through line 20. This condensate amounts to about 30% of the reaction product stream from reactor 14. The uncondensed gases, about 70% of the reaction product stream, comprising about 95% carbon dioxide, 3% lower hydrocarbons (i.e., less than 5 carbon atoms per molecule) and 2% hydrogen are passed through line 26 to the extractive carbon dioxide-volatile hydrocarbon separator, 27.

In separator 27, the carbon dioxide is first separated from the volatile hydrocarbons by absorption in aqueous monoethanolamine. The unabsorbed volatile hydrocarbons are removed via line 28. The carbon dioxide is regenerated by heating the absorbent solution to the boiling point and passing the resulting vapors through a condenser in separator 27 to liquify the water which is returned to the monoethanolamine solution. The resulting relatively dry carbon dioxide in line 5 is then recycled to the oxidizer 2 via the multiple heat exchanger 6, after removal of excess carbon dioxide via line 30.

The condensate from condenser 15 is passed via line 20 to phase separator 23. In phase separator 23 a hydrocarbon product having more than 4 carbon atoms in about 30% yield based on carbon monoxide entering reactor 14, is removed via line 24. Any excess water is removed through line 25.

Similar results are obtained when an iron catalyst is used in reactor 14. However in this case half of the steam in vaporizer 12 must be vented through line 29 to give in line 22 a second reactor feed in which the water does not exceed the 3:1 carbon monoxide:water ratio. The catalyst is an iron-copper catalyst, alkalized with potassium carbonate and containing 100 parts of iron, 0.1 part of copper and 0.25 parts of potassium carbonate. This catalyst is activated by heating to 270° C. and passing carbon monoxide over it for 24 hours at atmospheric pressure and a space velocity of 100/hr. Then hydrogen is passed over it under the same conditions and for the same amount of time.

Figure 5:
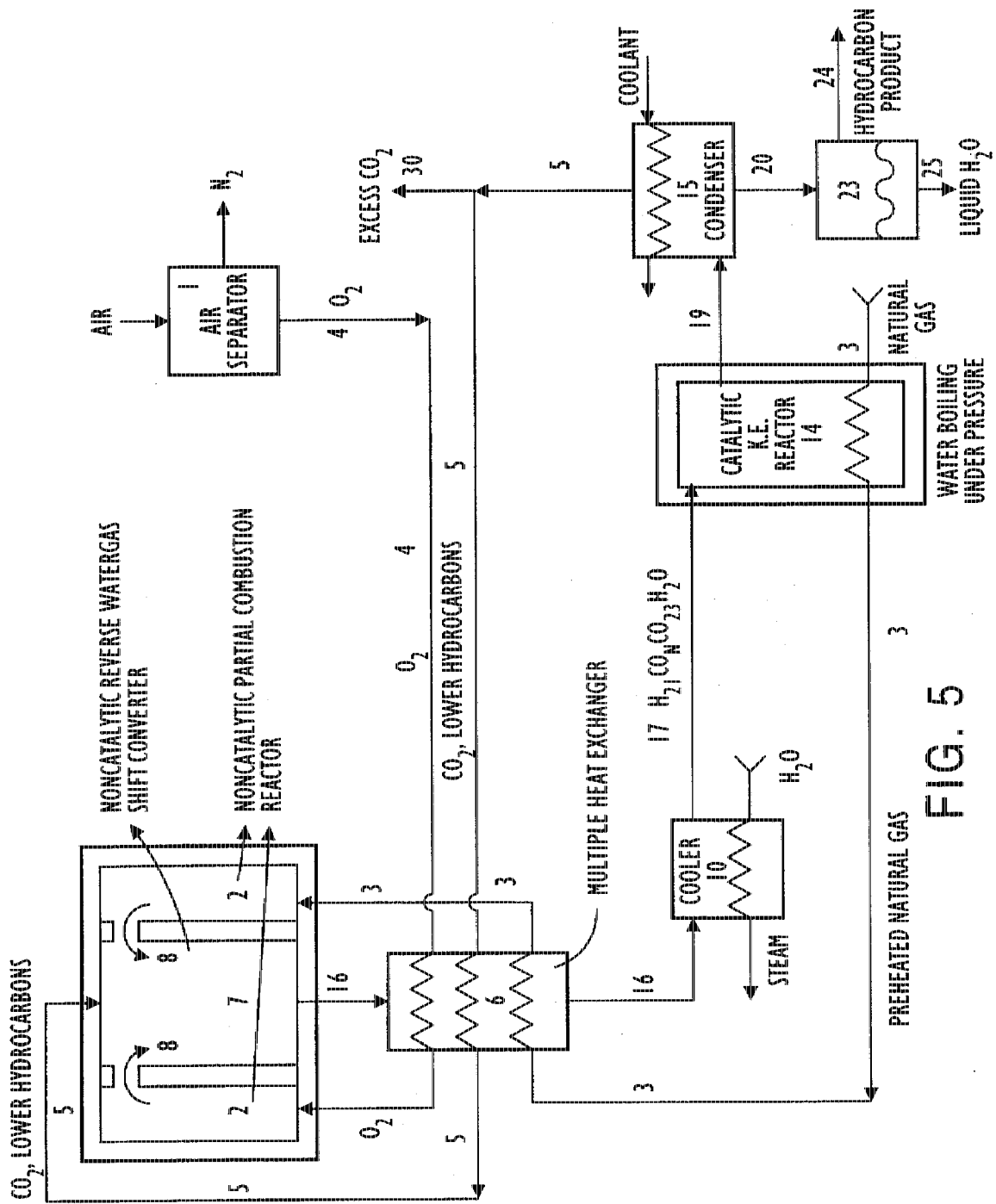
FIG. 5 is a detailed flow diagram of the preferred process reacting 2 moles of carbon dioxide with one mole of hydrogen in a first reactor while feeding essentially pure methane to the oxidizer.

The preferred embodiment of the present invention is illustrated in the accompanying schematic drawing, FIG. 5. In this example, the first reactor is maintained at a 2.5:1 ratio of carbon dioxide:hydrogen. The second reactor is charged with an activated cobalt catalyst. Referring now to FIG. 5, the following discussion describes the manufacture of multicarbon hydrocarbons by applying the process of the instant invention to a natural gas consisting of 100% methane.

Oxygen is separated from air in reactor 1, utilizing the composite mixed conductor membranes process of Thorogood et al. (U.S. Pat. No. 5,240,480) to give 95+% pure oxygen which is removed via line 4 and charged to reactor 2. Natural gas, essentially pure methane, is fed into the system via line 3 and is heated to about 900° C. by passing through reactor 14 and multiple heat exchanger 6. The oxygen and heated natural gas in volumetric ratio of about 0.5 are introduced into noncatalytic partial combustion reactor 2 operating at a temperature of 1300° C. under a pressure of 10 atmospheres. At the same time, carbon dioxide from condenser 15 is returned to oxidizer 2 via line 5 after passing through the multiple heat exchanger 6.

The concentric oxidizer/reverse water gas shift reactor combination described in FIG. 4 is used in this example. The outer reactor being the partial oxidation zone and the inner reactor being the Reverse Water Gas Shift Reaction zone as shown in FIG. 4, vessels 2 and 7.

The effluent from oxidizer 2, carbon monoxide, hydrogen and returned carbon dioxide are passed into the Reverse Water Gas Shift converter 7, via ports 8. The converter 7 is maintained at a temperature of 1300° C. by the heat generated in the partial oxidation reaction occurring in the surrounding reactor 2. In vessel 7 the hydrogen:carbon dioxide ratio is 1:2.5.

The product stream from reactor 7 in line 16 has the following composition: carbon monoxide=31%, carbon dioxide=44%, hydrogen=6% and water=19%. It is cooled by passing through the multiple heat exchanger 6 and cooler, 10. In this cooler, the temperature of the gaseous stream is reduced to about 300° C. This mixture is charged through line 17 to the Koelbel-Engelhardt reactor, 14 at a space velocity of about 30 per hour. Reactor 14 is maintained at 230° C. and 10 atmospheres. Reactor 14 is kept at the desired temperature by boiling water under pressure in a reactor jacket.

Reactor 14 is charged with a cobalt-thorium oxide-magnesium oxide-silicon dioxide catalyst containing 100 parts of cobalt, 5 parts of thorium, 10 parts of magnesium and 100 parts of silica. The catalyst is activated by heating for two hours at 450° C., with hydrogen gas passing over it at a space velocity of 1000/hr.

When steady state conditions are reached in reactor 14, samples of reactor effluent show a total conversion of carbon monoxide of about 98%. Gas chromatographic analysis shows that the hydrocarbon portion contains over 95% hydrocarbons having more than 4 carbon atoms.

The reaction product stream from reactor 14 is passed into condenser 15 via line 19. In this condenser, the temperature of the reaction product is lowered to 5° C., causing the hydrocarbons having more than 4 carbon atoms and the water present to condense and pass out of the condenser through line 20. This condensate amounts to about 30% of the reaction product stream from reactor 14. The uncondensed gases, about 70% of the reaction product stream, comprising about 95% carbon dioxide, 3% lower hydrocarbons (i.e., less than 5 carbon atoms per molecule) and 2% hydrogen are returned to the oxidizer 2 via heat exchanger 6 through line 5.

The condensate from condenser 15 is passed via line 20 to phase separator 23. In phase separator 23 a hydrocarbon product having more than 4 carbon atoms in about 30% yield based on carbon monoxide entering reactor 14, is removed via line 24. Any excess water is removed through line 25.

It is evident from the above description that the subject process provides for many advantages in the utilization of natural gas for the production of multicarbon hydrocarbons, which are liquid at room temperature and may serve as a mobile fuel, and may be further processed to provide gasoline or other fuel or feedstock for the production of high value chemicals. The subject process is highly efficient in the transformation of methane to higher aliphatics, in its utilization of thermal energy and its adaptability to a wide variety of natural gas compositions as a feedstock. In addition, the subject process combines well known processes in a novel way, so that the individual steps may utilize the technology which has been developed in association with these individual stages to optimize the process.

All publications mentioned in this specification testify to the skills of those engaged in the art and science to which this invention pertains, and all are incorporated by reference herein just as if each individual publication was singled out for incorporation by reference.

The invention now having been fully described and the results of its use set forth, it will be apparent to one of ordinary skill in the art that many changes and modifications can be made thereto without departing from the spirit or scope of the appended claims.

What is claimed is:

1. A process for the production of multicarbon hydrocarbons from a mixture of hydrogen and carbon monoxide gases, comprising the steps of:

(a) heating in a first reactor said mixture of gases with carbon dioxide in a molar ratio of carbon dioxide to hydrogen in the range of from about 4:1 to 1:1 at a temperature sufficient to attain a reverse water-gas shift reaction in said first reactor to produce additional carbon monoxide and water in a first reactor effluent;

(b) contacting in a second reactor said first reactor effluent with a metal catalyst at a temperature above about 150° C. wherein the carbon monoxide and water react to produce a second reactor effluent comprising multicarbon hydrocarbons, water and carbon dioxide; and (c) separating said second reactor effluent into a multicarbon hydrocarbon stream, a water stream and a carbon dioxide stream and returning a sufficient portion of said carbon dioxide stream to said first reactor to assist in maintaining the molar ratio of carbon dioxide to hydrogen in the range of from about 4:1 to 1:1 in said first reactor.

2. A process according to claim 1 in which the temperature of step b is lower than the temperature of step a and the first reactor effluent is cooled before contacting the metal catalyst in the second reactor.

3. A process according to claim 2 in which the first reactor effluent is cooled to a temperature about equal to that in the second reactor.

4. A process according to claim 1 in which said mixture of hydrogen and carbon monoxide gases is produced by oxidizing natural gas in a partial oxidizer.

5. A process according to claim 4 in which said carbon dioxide is returned to the first reactor via said partial oxidizer.

6. A process according to claim 1 in which the temperature in the first reactor is within the range of 800° C. to 2100° C.

7. A process according to claim 1 in which the temperature in the second reactor is within the range of 150° to 400° C.

8. A process according to claim 1 in which the metal catalyst in the second reactor is a Fischer-Tropsch catalyst.

9. A process according to claim 8 in which the metal catalyst is chosen from the group consisting of cobalt, nickel, manganese, and alloys thereof.

10. A process according to claim 1 in which prior to step (b) the first reactor effluent is separated into a hydrogen-enriched stream which is recycled to the first reactor and a hydrogen-depleted first reactor effluent which is subjected to said contacting in step (b) in the second reactor.

11. A process according to claim 1 in which the multicarbon hydrocarbons of said multicarbon hydrocarbon stream are separated into a lower boiling portion and into a higher boiling portion.

12. A process according to claim 11 in which the lower boiling portion contains hydrocarbons having less than 5 carbon atoms per molecule.

13. A process according to claim 12 in which said mixture of hydrogen and carbon monoxide gases is produced by oxidizing natural gas in a partial oxidizer and in which the lower boiling portion is returned to the partial oxidizer.

14. A process according to claim 12 in which the lower boiling portion is contacted with a polymerization catalyst to produce additional higher boiling hydrocarbons.

15. A process for the production of multicarbon hydrocarbons from a mixture of hydrogen and carbon monoxide gases, comprising the steps of:

(a) heating in a first reactor said mixture of gases with carbon dioxide in a molar ratio of carbon dioxide to hydrogen in the range of from about 4:1 to 1:1 at a temperature above about 800° C. to produce in a reverse water-gas shift reaction additional carbon monoxide and water in a first reactor effluent, (b) separating carbon monoxide and water from said first reactor effluent and recycling the remainder of said first reactor effluent to said first reactor;

(c) heating in a second reactor said separated carbon monoxide and at least 50% of said water separated from said first reactor effluent in the presence of a metal catalyst to react the carbon monoxide and water to produce a second reactor effluent comprising multicarbon hydrocarbons and carbon dioxide; and (d) separating said second reactor effluent into a multicarbon hydrocarbon stream and a carbon dioxide stream and returning a sufficient portion of said carbon dioxide stream to said first reactor to assist in maintaining the molar ratio of carbon dioxide to hydrogen in the molar ratio of about 4:1 to 1:1 in said first reactor.

16. A process according to claim 15 wherein the mixture of hydrogen and carbon monoxide gases is produced in a partial oxidizer.

17. A process according to claim 16 wherein said carbon dioxide returned from the second reactor effluent to said first reactor is through said partial oxidizer.

18. A process according to claim 15 which the metal catalyst in the second reactor is chosen from the group consisting of iron, cobalt, nickel, manganese and alloys thereof.

19. A process according to claim 15 in which the second reactor is maintained at a temperature in the range of 150° C. to 400° C.

20. A process according to claim 15 in which there is a stoichiometric excess of carbon dioxide in the first reactor.

21. A process according to claim 15 in which said multicarbon hydrocarbons from said second reactor effluent are separated into a lower boiling portion and a higher boiling portion.

22. A process according to claim 21 wherein said higher boiling portion is composed of multicarbon hydrocarbons having more than 4 carbon atoms per molecule.

23. A process according to claim 21 in which said mixture of hydrogen and carbon monoxide gases is produced by oxidizing natural gas in a partial oxidizer and in which said lower boiling portion is returned to the partial oxidizer.

24. A process according to claim 21 including the additional step of passing said lower boiling portion over a polymerization catalyst to produce additional higher boiling hydrocarbons.

25. A process for the production of liquid hydrocarbons from natural gas comprising the steps of:

(a) oxidizing said natural gas in a partial oxidizer to produce a syngas comprising hydrogen and carbon monoxide;

(b) heating said syngas at a temperature above about 800° C. in a first reactor with carbon dioxide at a molar ratio to hydrogen of from about 4:1 to 1:1 to produce water and additional carbon monoxide in a first reactor effluent;

(c) separating carbon monoxide and water from said first reactor effluent and recycling the remainder of said first reactor effluent to said first reactor;

(d) reacting in a second reactor said separated carbon monoxide with at least 50% of said separated water in the presence of a metal catalyst, wherein said metal catalyst catalyzes the reaction of carbon monoxide and water to produce a second reactor effluent comprising multicarbon hydrocarbons, carbon dioxide and water;

(e) separating liquid hydrocarbons and water from said second reactor effluent leaving a second reactor effluent remainder;

(f) returning at least a portion of said second reactor effluent remainder to said partial oxidizer; and (g) separating said liquid multicarbon hydrocarbon product from said water to provide an isolated liquid multicarbon hydrocarbon product.

26. A process according to claim 25 which the isolated liquid hydrocarbon product is a $C_{5+}$ fraction.

27. A process according to claim 25 in which the first reactor is maintained at a temperature in the range of about 800° to 1800° C. and at a pressure within the range of about 1 to 350 atmospheres.

28. A process according to claim 25 in which the second reactor is maintained at a temperature in the range of about 150° to 400° C. and at a pressure within the range of 1 to 100 atmospheres.

29. A process according to claim 25 in which the metal of the metal catalyst in the second reactor is chosen from the group consisting of iron, cobalt, nickel, manganese and alloys thereof.

30. A process according to claim 25 in which the portion of step (f) is at least 5%.

31. A process for producing multicarbon hydrocarbons from a mixture of gases including hydrogen and carbon monoxide produced from partial oxidation of natural gas, which comprises the steps of:

(a) heating in a first reactor said mixture of gases with carbon dioxide in a molar ratio to the hydrogen present in the range of about 4:1 to 1:1 at a temperature in the range of about 800° to about 1800° C. to produce a first reactor effluent comprising water and additional carbon monoxide;

(b) separating said carbon monoxide and water from said first reactor effluent and recycling the remainder of said first reactor effluent to said first reactor;

(c) reacting in a second reactor said separated carbon monoxide with at least 50% of said separated water at a temperature in the range of about 150° to about 300° C. and at a pressure in the range of about 1 to about 150 atm in contact with a metal catalyst selected from the group consisting of iron, cobalt, nickel, manganese and alloys thereof, wherein said metal catalyst catalyzes the reaction of carbon monoxide and water to produce a second reactor effluent comprising multicarbon hydrocarbons, carbon dioxide and water;

(d) separating liquid multicarbon hydrocarbons and water from said second reactor effluent leaving a second reactor effluent remainder; and (e) separating said liquid multicarbon hydrocarbon product from said water to provide an isolated liquid multicarbon hydrocarbon product.

32. The isolated liquid hydrocarbon product produced by the process of claim 31.

* * * * *